United States Patent [19]

Mihailovski et al.

[11] 4,008,318
[45] Feb. 15, 1977

[54] PHOSPHORYLATED THIOUREA FUNGICIDES

[75] Inventors: Alexander Mihailovski, Kensington; Don R. Baker, Orinda, both of Calif.

[73] Assignee: Stauffer Chemical Company, Westport, Conn.

[22] Filed: Aug. 25, 1975

[21] Appl. No.: 607,516

Related U.S. Application Data

[60] Continuation-in-part of Ser. No. 471,092, May 17, 1974, abandoned, which is a continuation of Ser. No. 335,415, Feb. 26, 1973, abandoned, which is a division of Ser. No. 336,110, Feb. 24, 1973, Pat. No. 3,847,980, which is a division of Ser. No. 213,714, Dec. 29, 1971, Pat. No. 3,767,734.

[52] U.S. Cl. ............................................. 424/211
[51] Int. Cl.² ........................................ A01N 9/36
[58] Field of Search .................... 424/211; 260/938

[56] References Cited
UNITED STATES PATENTS 3,291,866   12/1966   Mannes et al. ...................... 260/945
3,767,734   6/1973   Mihailovski et al. ............... 260/938

*Primary Examiner*—Leonard Schenkman
*Attorney, Agent, or Firm*—Daniel C. Block

[57] ABSTRACT

New compounds corresponding to the generic formula:

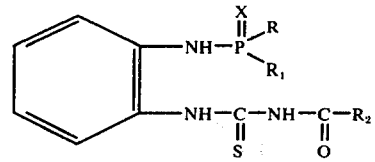

wherein X can be selected from oxygen and sulfur, R and $R_1$ can be the same or different and can be selected from lower alkyl and lower alkoxy, $R_2$ can be selected from lower alkyl, lower alkoxy and lower thioalkyl. The compounds are useful fungicides and biocides.

25 Claims, No Drawings

PHOSPHORYLATED THIOUREA FUNGICIDES

CROSS REFERENCE TO RELATED APPLICATIONS

This application is a continuation-in-part of application Ser. No. 471,092, filed May 17, 1974 now abandoned, which is a continuation of application Ser. No. 335,415, filed Feb. 26, 1973 now abandoned, which is a division of application Ser. No. 336,110, filed Feb. 24, 1973, now U.S. Pat. No. 3,847,980 issued Nov. 12, 1974, which is a division of application Ser. No. 213,714, filed Dec. 29, 1971 now U.S. Pat. No. 3,767,734, issued Oct. 23, 1973.

DESCRIPTION OF THE INVENTION

This invention is directed to a novel group of compounds which may be generally described as phosphorylated thioureas which are highly active fungicides and biocides. The compounds of the present invention are represented by the generic formula:

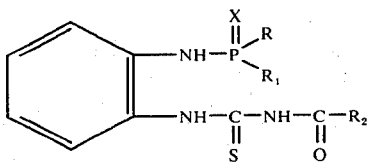

wherein X can be selected from oxygen and sulfur, R and $R_1$ can be the same or different and can be selected from lower alkyl and lower alkoxy, $R_2$ can be selected from lower alkyl, lower alkoxy and lower thioalkyl.

The above compounds can be prepared by phosphorylating o-phenylenediamine on one amino group, followed by treatment of the resulting phosphorylated aniline with a carbonyl isothiocyanate in an inert solvent such as acetone, benzene and the like. The products form rapidly and can be isolated in good purity from the solvent system.

In order to illustrate the merits of the present invention, the following examples are provided:

EXAMPLE 1

Preparation of 2-(3'-(methoxycarbonyl)-thioureido]-O,O-diethyl-phosphoranilide

Into a 500 ml., four-neck, round-bottom flask provided with paddle stirrer, thermometer and dropping funnel were placed 20.0 grams (0.185 mole) o-phenylenediamine, 18.8 grams (0.185 mole) triethylamine and 200 ml. of chloroform. To this mixture was then added 31.9 grams (0.185 mole) O,O-diethylphosphorochloridate dissolved in 40 ml. chloroform while the reaction temperature was maintained below 30° C. by cooling the flask in an ice bath. After the addition had been completed, the reagents were stirred for another 17 hours at room temperature. The resulting chloroform solution was washed twice with 100 ml. portions of water, dried and the solvent evaporated to give crude N-(2-aminophenyl)-O,O-diethylphosphoramidate. Upon recrystallization from carbon tetrachloride, 32.5 grams of this product were obtained. Then, 4.6 grams (0.019 mole) N-(2-amino-phenyl)-O,O-diethylphosphoramidate was dissolved in 30 ml. benzene. To this solution was added slowly 2.2 grams (0.019 mole) methoxycarbonyl isothiocyanate dissolved in 10 ml. benzene. The reaction mixture was stirred for about 16 hours at room temperature. A colorless precipitate formed. The solid was filtered and dried to yield 4.6 grams of 2-[3'-(methoxycarbonyl)-thioureido)-O,O-diethylphosphorylanilide, m.p. 154°–155° C. (dec.). Yield, 67% of theory.

EXAMPLE 2

Preparation of 2-[3'-(methoxycarbonyl)-thioureido]-O-ethyl-P-ethyl-thiophosphonanilide N-(2-aminophenyl)-O-ethyl-P-ethylthiphosphonoamidate was prepared from o-phenylenediamine and D-ethyl-p-ethylthiophosphonochloridate under conditions similar to those described for N-(2-aminophenyl)-O,O-diethyl in Example 1. To 5.0 grams (0.020 mole) N-(2-aminophenyl)-O-ethyl-P-ethylthiophosphonamidate in 20 ml. benzene was added a solution of 2.4 grams (0.020 mole) methoxycarbonyl isothiocyanate dissolved in 10 ml. benzene. The precipitated solid was filtered and dried to yield 5.6 grams of 2-[3'-(methoxycarbonyl)-thioureido]-O-ethyl-p-ethyl-thiophosphonanilide, m.p. 172°–173° C. (dec.). Yield, 76% of theory.

Other compounds were prepared in an analogous manner starting with the appropriate starting materials as outlined above. The following is a table of compounds representative of those embodied by the present invention. Compound numbers have been assigned to them and are used for identification throughout the balance of the specification.

TABLE I

| Compound No. | X | R | $R_1$ | $R_2$ |
|---|---|---|---|---|
| 1 | O | —CH$_2$CH$_3$ | —OCH$_2$CH$_3$ | —OCH$_3$ |
| 2 | O | —OCH$_2$CH$_3$ | —OCH$_2$CH$_3$ | —OCH$_3$ |
| 3 | O | —OCH$_2$CH$_3$ | —OCH$_2$CH$_3$ | —OCH$_2$CH$_3$ |
| 4 | O | —OCH$_2$CH$_3$ | —OCH$_2$CH$_3$ | —CH$_2$CH$_3$ |
| 5 | S | —CH$_2$CH$_3$ | —CH$_2$CH$_3$ | —OCH$_3$ |
| 6 | S | —CH$_2$CH$_3$ | —CH$_2$CH$_3$ | —OCH$_2$CH$_3$ |
| 7 | S | —CH$_2$CH$_3$ | —CH$_2$CH$_3$ | —CH$_3$ |
| 8 | S | —CH$_2$CH$_3$ | —OCH$_2$CH$_3$ | —OCH$_3$ |
| 9 | S | —CH$_2$CH$_3$ | —OCH$_2$CH$_3$ | —OCH$_2$CH$_3$ |
| 10 | S | —OCH$_2$CH$_3$ | —OCH$_2$CH$_3$ | —OCH$_3$ |
| 11 | S | —OCH$_2$CH$_3$ | —OCH$_2$CH$_3$ | —OCH$_2$CH$_3$ |
| 12 | O | —OCH$_2$CH$_3$ | —OCH$_2$CH$_3$ | —OCH$_2$CH$_2$CH$_3$ |
| 13 | S | —OCH$_2$CH$_3$ | —OCH$_2$CH$_3$ | —OCH$_2$CH$_2$CH$_3$ |
| 14 | S | —OCH$_2$CH$_3$ | —CH$_2$CH$_3$ | —OCH$_2$CH$_2$CH$_3$ |
| 15 | S | —OCH$_2$CH$_3$ | —OCH$_2$CH$_3$ | —CH$_3$ |
| 16 | S | —OCH$_2$CH$_3$ | —CH$_2$CH$_3$ | —CH$_3$ |
| 17 | S | —OCH$_2$CH$_3$ | —CH$_2$CH$_3$ | —SCH$_2$CH$_3$ |
| 18 | S | —OCH$_2$CH$_3$ | —CH$_2$CH$_3$ | —O—(CH$_2$)$_{15}$CH$_3$ |
| 19 | S | —OCH$_2$CH$_3$ | —CH$_2$CH$_3$ | —OCH$_2$CH(CH$_3$)$_2$ |
| 20 | O | —OCH$_2$CH$_3$ | —OCH$_2$CH$_3$ | —SCH$_2$CH$_3$ |
| 21 | O | —OCH$_2$CH$_3$ | —OCH$_2$CH$_3$ | —O—(CH$_2$)$_{15}$CH$_3$ |
| 22 | S | —OCH$_2$CH$_3$ | —OCH$_2$CH$_3$ | —OCH$_2$CH(CH$_3$)$_2$ |
| 23 | S | —OCH$_2$CH$_3$ | —OCH$_2$CH$_3$ | —OCH(CH$_3$)$_2$ |

TABLE I-continued

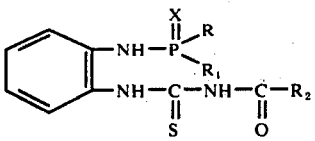

| Compound No. | X | R | R₁ | R₂ |
|---|---|---|---|---|
| 24 | S | —OCH₂CH₃ | —CH₂CH₃ | —OCH(CH₃)₂ |

FUNGICIDE TESTING PROCEDURES

A. Foliar Preventative Sprays

1. Bean Rust

The chemicals are dissolved in an appropriate solvent and diluted with water containing several drops of Tween 20, a wetting agent. Test concentrations, ranging from 1000 ppm downward, are sprayed to runoff on the primary leaves of pinto beans (*Phaseolus vulgaris* L.). After the leaves are dried, they are inoculated with a water suspension of spores of the bean rust fungus (*Uromyces phaseoli* Arthur) and the plants are placed in an environment of 100% humidity for 24 hours. The plants are then removed from the humidity chamber and held until disease pustules appear on the leaves. Effectiveness is recorded as the lowest concentration, in ppm, which will provide 50% reduction in pustule formation as compared to untreated, inoculated plants.

2. Bean Powdery Mildew

Test chemicals are prepared and applied in the same manner as for the bean rust test. After the plants are dry, the leaves are dusted with spores of the powdery mildew fungus (*Erysiphe polygoni* De Candolle) and the plants are retained in the greenhouse until the fungal growth appears on the leaf surface. Effectiveness is recorded as the lowest concentration, in ppm, which will provide 50% reduction in pustule formation as compared to untreated, inoculated plants.

3. Tomato Early Blight

Test chemicals are prepared and applied in the same manner as the bean rust and powdery mildew tests except that 4-week old tomato (*Lycopersicon esculentum*) plants are utilized as the host plant. When the leaves are dry, they are inoculated with a water suspension of spores of the early blight fungus (*Alternaris solani* Ellis and Martin) and placed in an environment of 100% humidity for 48 hours. The plants are then removed from the humidity chamber and held until disease lesions appear on the leaves. Effectiveness is recorded as the lowest concentration, in ppm, which will provide 50% reduction in number of lesions formed as compared to untreated, inoculated plants.

B. Tube Systemic Test

1. Bean Rust

The chemicals are dissolved in an appropriate solvent and diluted with tap water to a series of descending concentrations beginning at 50 ppm. Sixty ml. of each concentration are placed in a test tube. A pinto bean plant is placed in each tube and supported with a piece of cotton so that only the roots and lower stem are in contact with the test solution. Forty-eight hours later the bean leaves are inoculated with a water suspension of spores of the bean rust fungus and placed in an environment with 100% humidity for 24 hours. The plants are then removed from the humidity chamber and maintained in the greenhouse until the disease pustules appear on the leaves. Effectiveness is recorded as the lowest concentration, in ppm, which will provide 50% reduction in pustule formation as compared to untreated, inoculated plants.

2. Bean Powdery Mildew

Test chemicals are prepared and applied in the same manner as for the bean rust systemic test. After 2 days the leaves are dusted with spores of the powdery mildew fungus and maintained in greenhouse until mycelial growth appears on the leaf surfaces. Effectiveness is recorded as the lowest concentration, in ppm, which will provide a 50% reduction in mycelial growth on the leaf surface as compared to untreated, inoculated plants.

C. Systemic Soil Drench

1. Bean Rust

Pinto beans are grown in 1-pint ice cream cartons, each containing 1 lb. of soil. Aliquots of the toxicant, dissolved in an appropriate solvent, are diluted with 25 ml. of water and drenched onto the soil surface. Two days later the bean leaves are inoculated with a water suspension of spores of the rust fungus, and the plants are placed in an environment with 100% humidity for 24 hours. The plants are then removed from the humidity chamber and maintained in the greenhouse until the pustules appear on the leaves. Effectiveness is recorded as the minimum concentration, in ppm per lb. of soil, which will provide 50% reduction in number of pustules as compared to untreated inoculated plants.

2. Bean Powdery Mildew

The bean plants and chemicals are prepared and applied as in the rust systemic soil drench test. After ten days, the bean leaves are dusted with spores of the powdery mildew fungus and maintained in the greenhouse until the mycelial growth appears on the leaf surface. Effectiveness is recorded as the minimum concentration, in ppm per lb. of soil, which will provide 50% reduction in mycelial growth on the leaf surface in comparison to untreated, inoculated plants.

The results of these tests are tabulated in Table II.

TABLE II

| Compound No. | Foliar Spray | | | Tube Systemic | | Soil Drench | |
|---|---|---|---|---|---|---|---|
| | Rust | Mildew | Tomato Blight | Rust | Mildew | Rust | Mildew |
| 1 | 500 | 100 | >1000 | 25 | 0.5 | — | 6 |
| 2 | 100 | 25 | >1000 | 5 | 0.25 | 27 | 3 |
| 3 | 1000 | 25 | >1000 | — | 1 | — | 6 |
| 4 | >1000 | 100 | 1000 | — | 5 | — | >55 |

TABLE II-continued

| Compound No. | Foliar Spray Rust | Mildew | Tomato Blight | Tube Systemic Rust | Mildew | Soil Drench Rust | Mildew |
|---|---|---|---|---|---|---|---|
| 5 | 100 | 25 | 1000 | 5 | 0.13 | 27 | 6 |
| 6 | >1000 | 50 | >1000 | 10 | 1 | — | >55 |
| 7 | >1000 | 500 | — | 50 | 5 | — | >55 |
| 8 | 1000 | 10 | >1000 | 10 | 1 | — | >55 |
| 9 | >1000 | 25 | 1000 | 50 | 5 | — | |
| 10 | 100 | 10 | >1000 | 10 | 0.13 | — | >55 |
| 11 | 1000 | 25 | >1000 | 50 | 5 | — | |
| 12 | >1000 | 500 | — | — | 5 | — | |
| 13 | >1000 | 500 | — | — | >50 | — | — |
| 14 | >1000 | 25 | 1000 | — | >50 | — | — |
| 15 | >1000 | 1000 | — | — | 10 | — | — |
| 16 | >1000 | 500 | — | — | 5 | — | |
| 17 | >1000 | 1000 | — | — | — | — | — |
| 18 | >1000 | 1000 | — | — | — | — | |
| 19 | 1000 | 100 | >1000 | — | — | — | |
| 20 | >1000 | >1000 | — | — | — | — | — |
| 21 | >1000 | 1000 | — | — | — | — | — |
| 22 | >1000 | 500 | — | — | — | — | |
| 23 | 1000 | 100 | >1000 | — | — | — | |
| 24 | 1000 | 100 | >1000 | — | — | — | |

BIOCIDE TESTING PROCEDURES

Tubes of sterilized nutrient and malt extract broth are prepared. Aliquots of the toxicant, dissolved in an appropriate solvent, are injected through the stopper, into the broth, to provide concentrations ranging from 50 ppm downward. The test organisms consist of two fungi, *Aspergillus niger* (A.n.) van Tieghem and *Penicillium italicum* (P.i.) Wehmer, and two bacteria, *Escherichia coli* (E.c.) Migula and *Staphylococcus aereus* (S.a.) Rosenback. Three drops of a spore suspension of each of the fungi are injected into the tubes of malt broth and three drops of the bacteria are injected into the nutrient broth. One week later the growth of each organism is observed and effectiveness of the chemical is recorded as the lowest concentration in ppm which provides 50% inhibition of growth as compared to untreated inoculated tubes. The results of these tests are tabulated in Table III.

TABLE III

| Compound No. | A.n. | P.i. | E.c. | S.a. |
|---|---|---|---|---|
| 1 | >50 | 5 | >50 | >50 |
| 2 | >50 | (1) | >50 | >50 |
| 3 | >50 | (1) | >50 | >50 |
| 4 | >50 | (25) | >50 | >50 |
| 5 | >50 | (5) | >50 | >50 |
| 6 | >50 | (5) | >50 | >50 |
| 7 | >50 | >50 | >50 | >50 |
| 8 | >50 | 5 | >50 | >50 |
| 9 | >50 | 5 | >50 | >50 |
| 10 | >50 | (1) | >50 | >50 |
| 11 | >50 | 5 | >50 | >50 |
| 12 | >50 | 5 | >50 | >50 |
| 13 | >50 | 5 | >50 | >50 |
| 14 | >50 | 5 | >50 | >50 |
| 15 | >50 | >50 | >50 | >50 |
| 16 | >50 | >50 | >50 | >50 |
| 17 | >50 | 50 | >50 | |
| 18 | >50 | 5 | >50 | >50 |
| 19 | >50 | 25 | >50 | >50 |
| 20 | >50 | 50 | >50 | 50 |
| 21 | >50 | 10 | >50 | >50 |
| 22 | >50 | >50 | >50 | >50 |
| 23 | >50 | 25 | >50 | >50 |
| 24 | >50 | 50 | >50 | >50 |

( ) = partial control

The compounds of this invention are generally embodied into a form suitable for convenient application. For example, the compounds can be embodied into pesticidal composition which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite; diatomite; gypsum; clays, propellants, such as dichlorodifluoromethane, etc. If desired, however, the active compounds can be applied directly to feedstuffs, seeds, etc. upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise not more than about 15.0% by weight of the composition. Preferably, however, the pesticide compositions of this invention will be in the form of solutions or suspensions containing about 0.1 to 1.0% by weight of the active pesticide compound.

As can be observed from the data in Tables II and III, the compounds of this invention are selectively active on *Penicillium italicum* and *Erysiphe polygone* (powdery mildew). Also, field test data indicates that Compound No. 10 controls apple scab (*Venturia inaequalis*) when applied at 2.25 lbs. a.i./acre.

What is claimed is:

1. A method of selectively controlling fungi selected from the group consisting of *Penicillium italicum* and *Erysiphe polygone* comprising contacting the habitat thereof with a fungicidally effective amount of a compound corresponding to the formula:

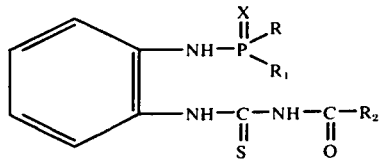

wherein X is selected from the group consisting of oxygen and sulfur, R and $R_1$ can be the same or different and are selected from the group consisting of lower alkyl having 1–4 carbon atoms and lower alkoxy having 1–4 carbon atoms, $R_2$ is selected from the group consisting of lower alkyl, lower alkoxy and lower thioalkyl each having from 1–4 carbon atoms.

When used in this application, the terms lower alkyl, lower alkoxy and lower thioalkyl refer to straight or branched chain groups having from 1 to 4 carbon atoms.

2. A method as set forth in claim 1 wherein X is oxygen, R is —$CH_2CH_3$, $R_1$ is —$OCH_2CH_3$ and $R_2$ is —$OCH_3$.

3. A method as set forth in claim 1 wherein X is oxygen, R is —$OCH_2CH_3$, $R_1$ is —$OCH_2CH_3$ and $R_2$ is —$OCH_3$.

4. A method as set forth in claim 1 wherein X is oxygen, R is —$OCH_2CH_3$, $R_1$ is —$OCH_2CH_3$ and $R_2$ is —$OCH_2CH_3$.

5. A method as set forth in claim 1 wherein X is oxygen, R is —$OCH_2CH_3$, $R_1$ is —$OCH_2CH_3$ and $R_2$ is —$CH_2CH_3$.

6. A method as set forth in claim 1 wherein X is sulfur, R is —$CH_2CH_3$, $R_1$ is —$CH_2CH_3$ and $R_2$ is —$OCH_3$.

7. A method as set forth in claim 1 wherein X is sulfur, R is —$CH_2CH_3$, $R_1$ is —$CH_2CH_3$ and $R_2$ is —$OCH_2CH_3$.

8. A method as set forth in claim 1 wherein X is sulfur, R is —$CH_2CH_3$, $R_1$ is —$CH_2CH_3$ and $R_2$ is —$CH_3$.

9. A method as set forth in claim 1 wherein X is sulfur, R is —$CH_2CH_3$, $R_1$ is —$OCH_2CH_3$ and $R_2$ is —$OCH_3$.

10. A method as set forth in claim 1 wherein X is sulfur, R is —$CH_2CH_3$, $R_1$ is —$OCH_2CH_3$ and $R_2$ is —$OCH_2CH_3$.

11. A method as set forth in claim 1 wherein X is sulfur, R is —$OCH_2CH_3$, $R_1$ is —$OCH_2CH_3$ and $R_2$ is —$OCH_2CH_3$.

12. A method as set forth in claim 1 wherein X is oxygen, R is —$OCH_2CH_3$, $R_1$ is —$OCH_2CH_3$ and $R_2$ is —$OCH_2CH_2CH_3$.

13. A method as set forth in claim 1 wherein X is sulfur, R is —$OCH_2CH_3$, $R_1$ is —$OCH_2CH_3$ and $R_2$ is —$OCH_2CH_2CH_3$.

14. A method as set forth in claim 1 wherein X is sulfur, R is —$OCH_2CH_3$, $R_1$ is —$CH_2CH_3$ and $R_2$ is —$OCH_2CH_2CH_3$.

15. A method as set forth in claim 1 wherein X is sulfur, R is —$OCH_2CH_3$, $R_1$ is —$OCH_2CH_3$ and $R_2$ is —$CH_3$.

16. A method as set forth in claim 1 wherein X is sulfur, R is —$OCh_2CH_3$, $R_1$ is —$CH_2CH_3$ and $R_2$ is —$CH_3$.

17. A method as set forth in claim 1 wherein X is sulfur, R is —$OCH_2CH_3$, $R_1$ is —$CH_2CH_3$ and $R_2$ is —$SCH_2CH_3$.

18. A method as set forth in claim 1 wherein X is sulfur, R is —$OCH_2CH_3$, $R_1$ is —$CH_2CH_3$ and $R_2$ is —O—$(CH_2)_3$ $CH_3$.

19. A method as set forth in claim 1 wherein X is sulfur, R is —$OCH_2CH_3$, $R_1$ is —$CH_2CH_3$ and $R_2$ is

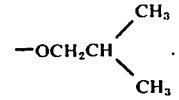

20. A method as set forth in claim 1 wherein X is oxygen, R is —$OCH_2CH_3$, $R_1$ is —$OCH_2CH_3$ and $R_2$ is —$SCH_2CH_3$.

21. A method as set forth in claim 1 wherein X is oxygen, R is —$OCH_2CH_3$, $R_1$ is —$OCH_2CH_3$ and $R_2$ is —O—$(CH_2)_3$ $CH_3$.

22. A method as set forth in claim 1 wherein X is sulfur, R is —$OCH_2CH_3$, $R_1$ is —$OCH_2CH_3$ and $R_2$ is

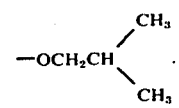

23. A method as set forth in claim 1 wherein X is sulfur, R is —$OCH_2CH_3$, $R_1$ is —$OCH_2CH_3$ and $R_2$ is

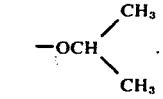

24. A method as set forth in claim 1 wherein X is sulfur, R is —$OCH_2CH_3$, $R_1$ is —$CH_2CH_3$ and $R_2$ is

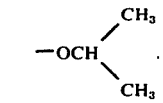

25. A method of selectively controlling fungi selected from the group consisting of *Penicillium italicum*, *Erysiphe polygone* and *Venturia inaequalis* comprising contacting the habitat thereof with a fungicidally effective amount of a compound corresponding to the formula:

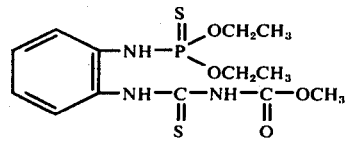

* * * * *

UNITED STATES PATENT AND TRADEMARK OFFICE
CERTIFICATE OF CORRECTION

PATENT NO. : 4,008,318
DATED : February 15, 1977
INVENTOR(S) : Alexander Mihailovski et al.

It is certified that error appears in the above-identified patent and that said Letters Patent are hereby corrected as shown below:

Column 1, line 46, the portion of the title reading "2-(3'-" should read ---2-[3'---.

Column 2, line 13, the word reading "ethylthiphos-" should read ---ethylthiophos- ---.

Column 2, line 15, the word reading "D-ethyl" should read ---O-ethyl---.

Column 2, line 17, the word reading "diethyl" should read ---diethylphosphoramidate---.

Column 5, line 33, the word reading "Rosenback" should read ---Rosenbach---.

Signed and Sealed this

Twenty-ninth Day of November 1977

[SEAL]

Attest:

RUTH C. MASON
*Attesting Officer*

LUTRELLE F. PARKER
*Acting Commissioner of Patents and Trademarks*